United States Patent
Austria (10) Patent No.: US 10,201,369 B2
(45) Date of Patent: *Feb. 12, 2019

(54) SCALPEL HANDLE SHEATH WITH BLADE REMOVER

(71) Applicant: Aspen Surgical Products, Inc., Caledonia, MI (US)

(72) Inventor: Georgene Austria, West Hills, CA (US)

(73) Assignee: Aspen Surgical Products, Inc., Caledonia, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/604,981

(22) Filed: May 25, 2017

(65) Prior Publication Data

US 2017/0258485 A1    Sep. 14, 2017

Related U.S. Application Data

(63) Continuation of application No. 14/640,327, filed on Mar. 6, 2015, now Pat. No. 9,693,797.

(60) Provisional application No. 61/966,996, filed on Mar. 7, 2014.

(51) Int. Cl.
| | |
|---|---|
| *A61B 17/3213* | (2006.01) |
| *A61B 17/3217* | (2006.01) |
| *A61B 17/3215* | (2006.01) |
| *A61B 17/3211* | (2006.01) |

(52) U.S. Cl.
CPC ...... *A61B 17/3213* (2013.01); *A61B 17/3217* (2013.01); *A61B 17/3215* (2013.01); *A61B 2017/32113* (2013.01)

(58) Field of Classification Search
CPC ............ A61B 17/3213; A61B 17/3215; A61B 17/3217; A61B 17/3211; A61B 2017/32113

USPC ............................ 30/340, 151, 162; 606/167
See application file for complete search history.

(56) References Cited

U.S. PATENT DOCUMENTS

| | | | |
|---|---|---|---|
| 3,921,289 | A | 11/1975 | Hasegawa |
| 4,173,071 | A | 11/1979 | Ishida |
| 4,998,334 | A | 3/1991 | Pemberton et al. |
| 5,868,771 | A | 2/1999 | Herbert et al. |
| 6,757,977 | B2 | 7/2004 | Dambal et al. |

(Continued)

FOREIGN PATENT DOCUMENTS

| | | |
|---|---|---|
| AU | 620691 B | 8/1992 |
| GB | 846877 A | 8/1960 |

(Continued)

OTHER PUBLICATIONS

European Search Report dated May 20, 2015; Application No. 15158070.1-1659; pp. 1-4.

*Primary Examiner* — Phong Nguyen
(74) *Attorney, Agent, or Firm* — Price Heneveld LLP (57) ABSTRACT

A scalpel handle sheath includes a body defining a first end and an arm adjacent the first end, the flexible arm having a first boss extending inwardly therefrom and a second boss extending outwardly from the arm. The scalpel handle sheath also includes a shield coupled with the body and slideable between a retracted position and a removal position. The shield defines an edge applying an inward force on the second boss during movement of the shield from the extended position to the removal position and a removal flange extending within the shield and passing the first end of the body during movement of the shield into the removal position.

6 Claims, 7 Drawing Sheets

(56) References Cited

U.S. PATENT DOCUMENTS

| | | |
|---|---|---|
| D542,415 S | 5/2007 | Sandel |
| D568,475 S | 5/2008 | Sandel et al. |
| 8,898,910 B2 | 12/2014 | Ichiyanagi et al. |
| 2004/0186496 A1 | 9/2004 | Sandel et al. |
| 2007/0265651 A1 | 11/2007 | Yi et al. |
| 2009/0192538 A1 | 7/2009 | Sandel et al. |
| 2010/0137894 A1 | 6/2010 | Ueno et al. |
| 2012/0083816 A1 | 4/2012 | Austria |
| 2012/0311869 A1 | 12/2012 | Ichiyanagi et al. |
| 2013/0079804 A1 | 3/2013 | Milton et al. |
| 2013/0245656 A1 | 9/2013 | Austria |

FOREIGN PATENT DOCUMENTS

| | | |
|---|---|---|
| GB | 2464751 B | 5/2012 |
| JP | 3026909 B2 | 3/2000 |
| JP | 3126664 B2 | 1/2001 |
| JP | 2002177291 A | 6/2002 |
| JP | 2006340857 A | 12/2006 |
| JP | 5390694 B2 | 1/2014 |
| WO | 2008132762 A1 | 11/2008 |
| WO | 2011108099 A1 | 9/2011 |
| WO | 2012002910 A1 | 1/2012 |

SCALPEL HANDLE SHEATH WITH BLADE REMOVER

CROSS-REFERENCE TO RELATED APPLICATION

This application is a continuation of U.S. application Ser. No. 14/640,327, filed on Mar. 6, 2015, entitled "SCALPEL HANDLE SHEATH WITH BLADE REMOVER," now U.S. Pat. No. 9,693,797, the disclosure of which is hereby incorporated herein by reference in its entirety. U.S. application Ser. No. 14/640,327 claims priority to U.S. Provisional Application No. 61/966,996, filed on Mar. 7, 2014, entitled "SCALPEL HANDLE SHEATH WITH BLADE REMOVER," the disclosure of which is hereby incorporated herein by reference in its entirety.

TECHNOLOGICAL FIELD

The present disclosure relates generally to a holder for scalpel handles. In particular the sheath can receive a reusable scalpel and handle in an assembly that functions as a safety scalpel handle.

BACKGROUND

Accidental cuts or punctures may occur due to sharp instruments, either during use, during transfer from one person to another, or from inadvertent misplacement thereof in potentially dangerous locations. Such injuries are particularly dangerous in the medical arena, as diseases can be spread through accidental contact with "sharps," including scalpel blades or the like. In particular, scalpels may include a reusable handle that can be assembled with a disposable blade. Such handles may not include any protection from contact with the blade when assembled thereto and, further, may present additional opportunity for injury during removal of a to-be-disposed blade prior to reuse of the handle.

Accordingly, further advances in protection from injury due to inadvertent contact with scalpel blades, including during removal, are desired.

SUMMARY

According to one aspect of the disclosure, a scalpel handle sheath includes a body defining a first end and an arm adjacent the first end, the arm having a first boss extending inwardly therefrom and a second boss extending outwardly from the arm. The scalpel handle sheath also includes a shield coupled with the body and slideable between a retracted position and a removal position. The shield defines an edge applying an inward force on the second boss during movement of the shield from the extended position to the removal position and a removal flange extending within the shield and passing the first end of the body during movement of the shield into the removal position.

According to another aspect of the disclosure, a surgical device assembly includes a sheath having a body defining a cavity open to a first end of the body and an arm adjacent the first end, the arm having a first boss extending inwardly therefrom, and a shield coupled with the body and slideable between a retracted position and a removal position. The shield defines an edge applying an inward force on the second boss during movement of the shield from the extended position to the removal position and a removal flange extending within the shield and passing the first end of the body during movement of the shield into the removal position. The surgical device assembly further includes a scalpel including a handle received within the cavity.

According to another aspect of the disclosure, a scalpel handle sheath includes a body defining a first end and an arm adjacent the first end with a first boss extending laterally from the arm and a shield coupled with the body and slideable between a retracted position and a removal position. The shield defines an edge applying an inward force on the flexible arm during movement of the shield from toward the retracted position to the removal position and a removal flange extending within the shield and passing the first end of the body during movement of the shield from the toward retracted position to the removal position.

In an example, the body may further define a second boss extending outwardly from the arm. In such an example the shield may be further slideable through an extended position between the retracted position and the removal position and may define a clearance track receiving the second boss therein during sliding of the shield from the retracted position to the extended position. The edge of the shield may be defined on an end of the clearance track positionable adjacent the second boss when the shield is in the extended position.

These and other features, advantages, and objects of the present device will be further understood and appreciated by those skilled in the art upon studying the following specification, claims, and appended drawings.

DETAILED DESCRIPTION OF EMBODIMENTS

Figure 1:
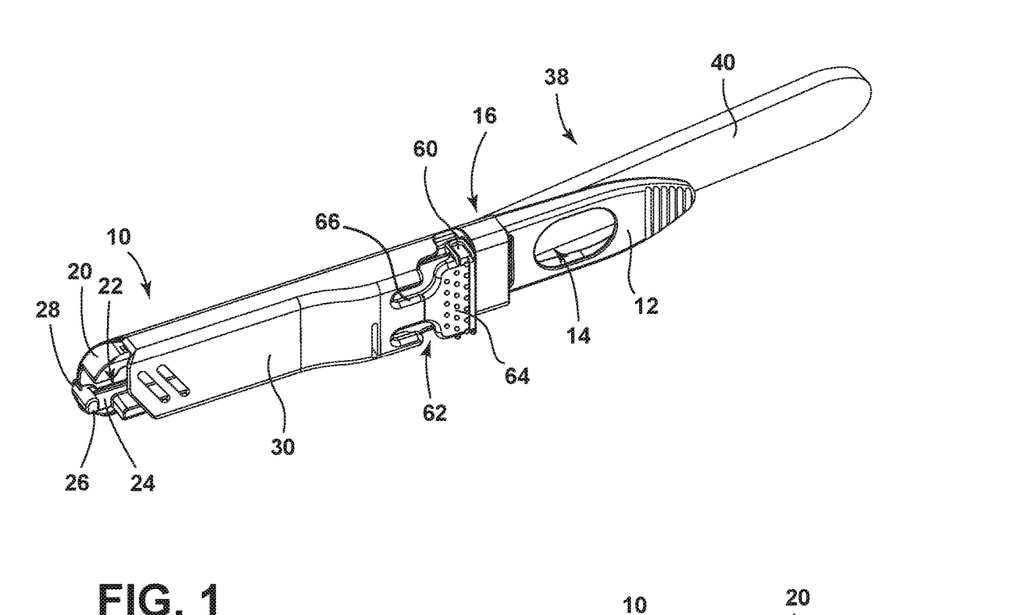
FIG. 1 is a front-right perspective view of a scalpel handle sheath during assembly thereof with a scalpel.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-4, reference numeral 10 generally designates a scalpel handle sheath, which may simply be referred to as a "sheath." The sheath 10 includes a body 12 defining a handle-receiving cavity 14 open on at least a first side 16 of the body 12 at an insertion opening 18. The receiving cavity 14 is further open to a first end 20 of the body through a narrowed sleeve region 22 remote from the insertion opening 18. The body 12 further defines a flexible arm 24 adjacent the first end 20 with a first boss 26 extending inwardly therefrom adjacent the sleeve region 22 and a second boss 28 extending outwardly from the arm 24. The sheath 10 further includes a shield 30 coupled with the body 12 and slideable between a retracted position (FIGS. 3 and 4) and a removal position (shown in FIG. 11) with an intermediate extended position (shown in FIGS. 6A and 10) therebetween. The shield 30 defines a clearance track 32 receiving the second boss 28 therein during sliding of the shield 30 from the retracted position to the extended position. An edge 34 of the clearance track 32 applies an inward force on the second boss 28 during movement of the shield 30 from the extended position to the removal position. The shield further defines a removal flange 36 extending within the shield 30 and passing the first end 20 of the body 12 during movement of the shield 30 from the extended position to the removal position.

Figure 2:
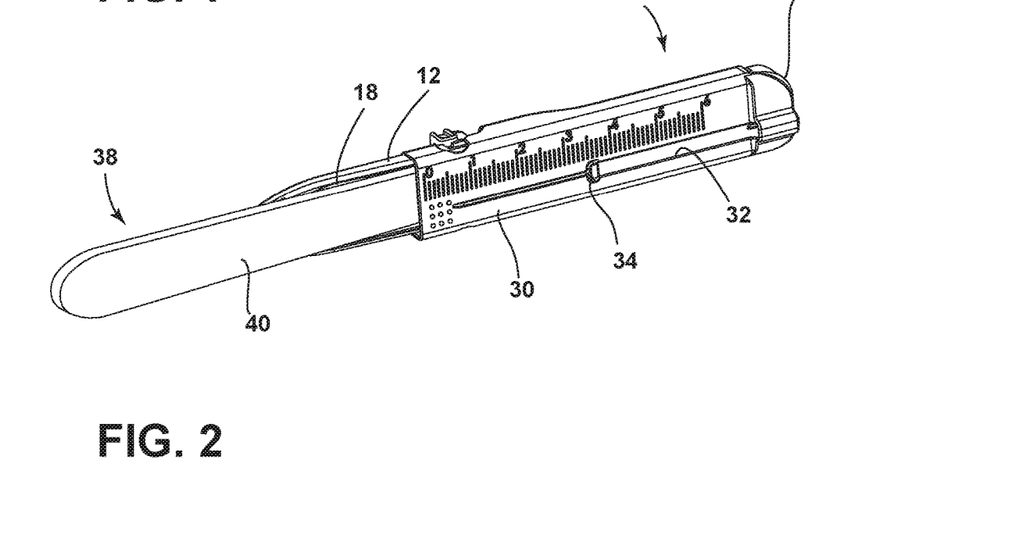
FIG. 2 is a back-left perspective view of the scalpel handle sheath of FIG. 1 during assembly thereof with a scalpel.
Figure 8:
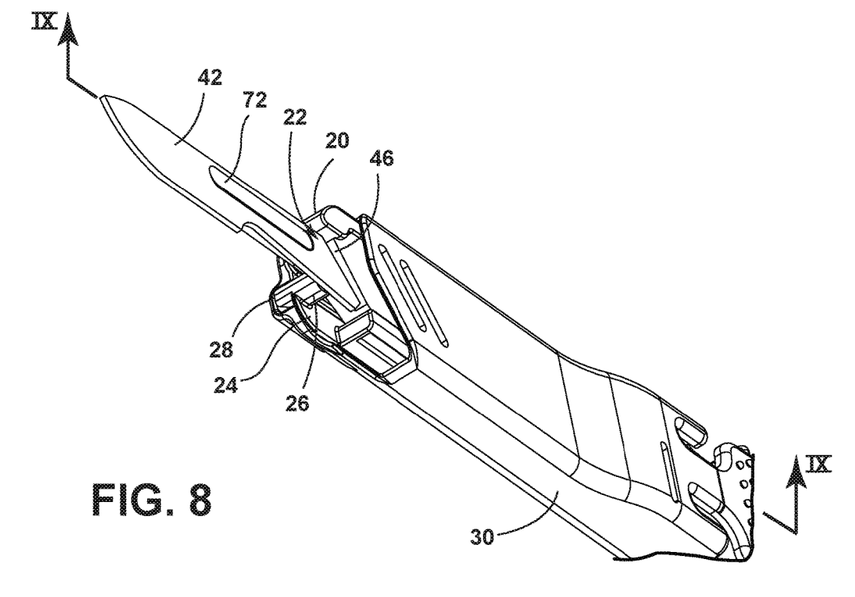
FIG. 8 is a front-bottom perspective view of the assembly of FIG. 7.

As shown in FIGS. 1 and 2, the sheath 10 may be assembled with a scalpel 38. It is noted that the scalpel 38 shown is merely exemplary and that sheath 10 may receive a number of different scalpels including different handle 40 and blade 42 configurations and may function in the same manner described herein with such varied configurations. The scalpel 38 has a handle 40 and a blade 42 coupled with a holder end 44 of the handle. The scalpel handle 40 is removably received within the cavity 14 with the holder end 44 extending through the sleeve region 22 such that the blade 42 extends from the first end 20 of the body 12. When scalpel 38 is assembled with sheath 10 as such, the first boss 26 extends inwardly to adjacent a portion of the blade 42 (as shown in FIG. 8), which may be subsequently assembled onto holder end 44. Further, when assembled, the blade 42 may be exposed when the shield 30 is in the retracted position and concealed when the shield 30 is in the extended position.

As shown in FIGS. 1 and 2, sheath 10 can be assembled onto the handle 40 of scalpel 38 (with blade 42 not present thereon) by inserting the handle 40 into the sheath 10. This insertion is achieved by sliding the holder end 44 into the insertion opening 18 of the body 12 until the handle 40 is fully seated and engaged within the cavity 14 of body 12. FIG. 1 shows the handle 40 being inserted from the rear side of the body 12 with the insertion direction of the handle 40 into position within cavity 14 being such that the holder end 44 is directed toward and through the sleeve region 22 so as to at least partially extend threrethrough and past first end 14 of body 12. FIG. 2 shows such insertion from a side 16 of the sheath on which insertion opening 18 is positioned. The handle 40 may be inserted while the shield 30 of the sheath 10 is in the extended position.

Figure 3:
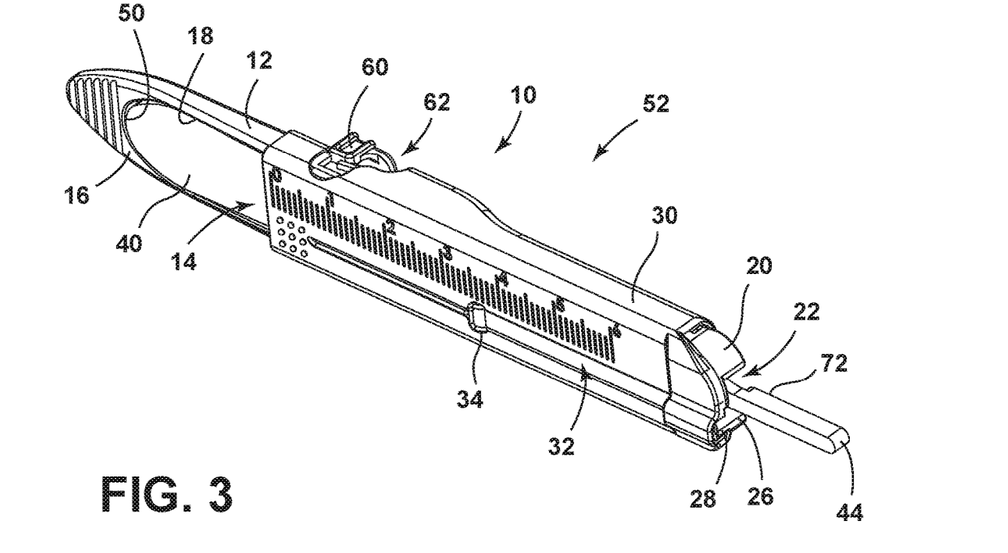
FIG. 3 is a front-left perspective view of the scalpel handle sheath of FIG. 1 in a retracted condition and assembled with a scalpel handle without a blade.
Figure 4:
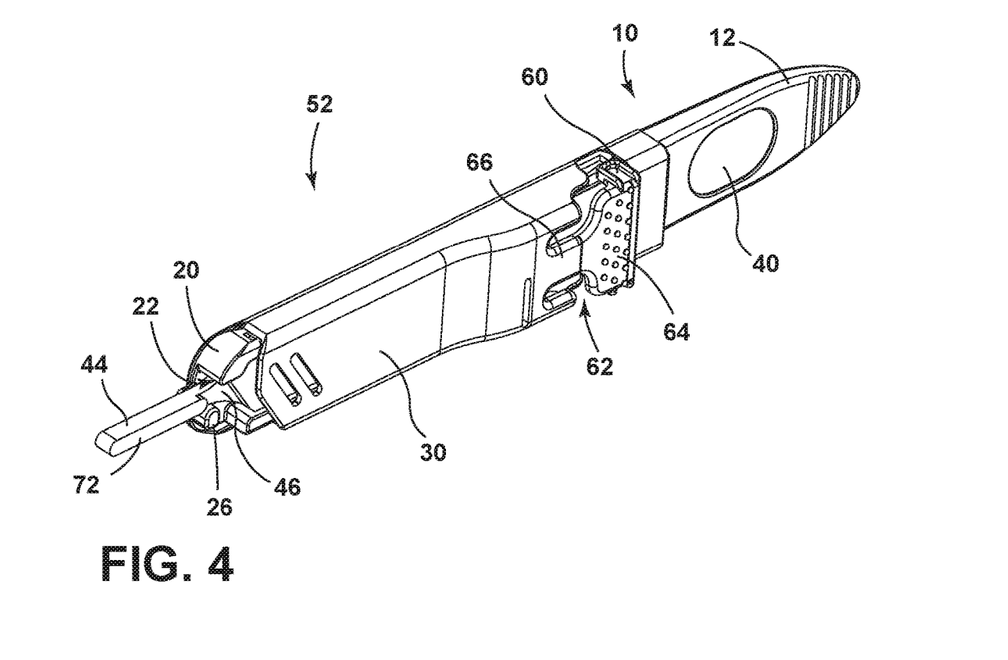
FIG. 4 is a front-right perspective view of the scalpel handle sheath of FIG. 1 in a retracted condition and assembled with a scalpel handle.

As the insertion of handle 40 into body 12 continues, the neck 46 of the handle 40 adjacent the holder end 44 rests at a junction of cavity 14 with sleeve region 22. Thus, sleeve region 22 prevents the handle 40 from sliding out from the sheath 10 during use. A second end 48 of the handle (opposite holder end 44) is then pressed to sit firmly inside the cavity 14 of body 12 body. A wall 50 of the cavity 14 may be configured to restrict movement of the handle 40 (such as by the incorporation of an undercut or the like corresponding to the shape of second end 48 of handle 40) during use of the resulting assembly 52, as shown in FIGS. 3 and 4. When assembly 52 is achieved, the shield 30 may then be pulled back to expose holder end 44 of handle 40 for assembly of blade 42 thereon.

Figures 5, 6A, 6B:
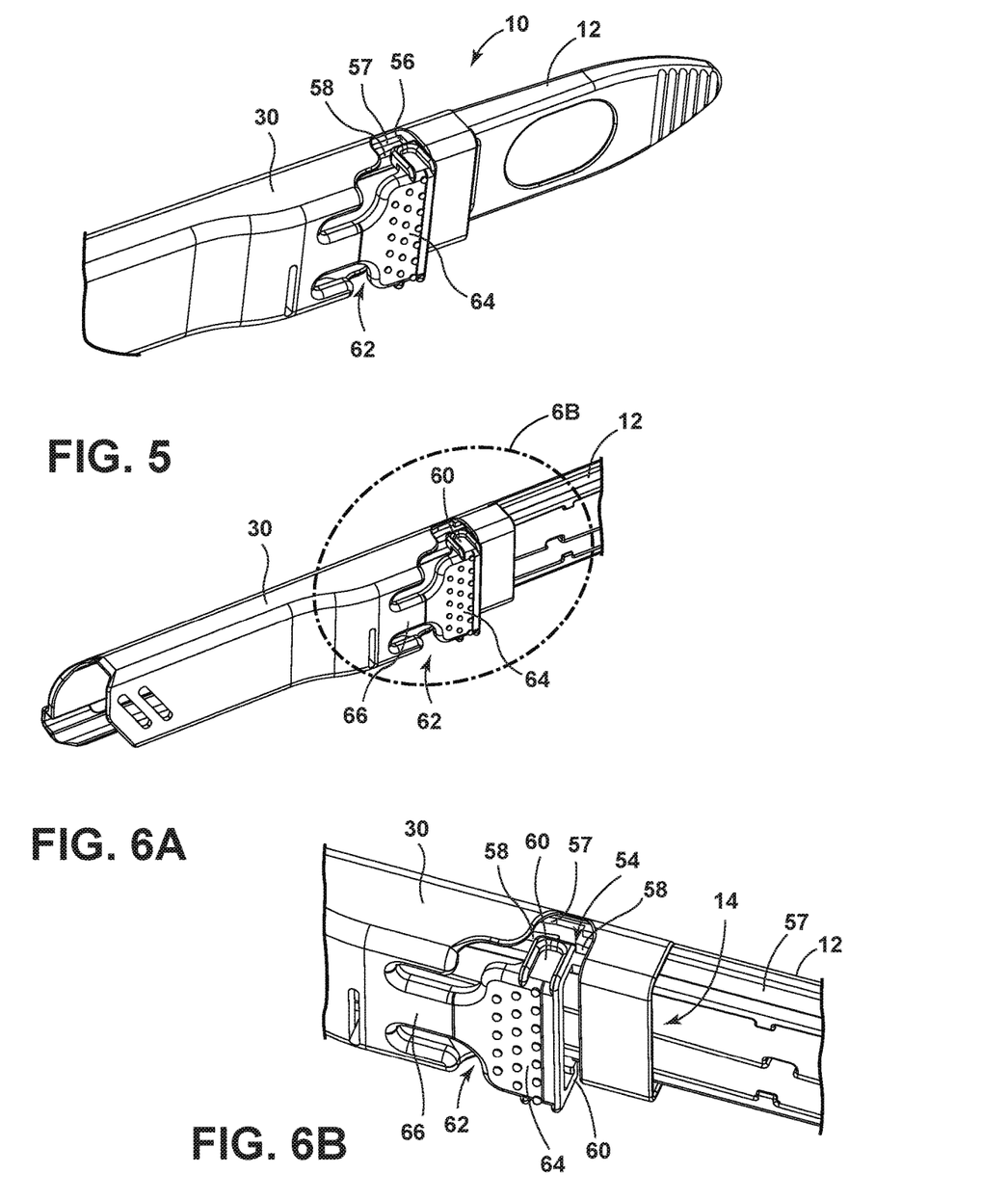
FIG. 5 is a partial view of the scalpel handle sheath of FIG. 1 in a retracted position showing a locking mechanism thereof.
FIG. 6A is a further partial view of the scalpel handle sheath of FIG. 1 in an extended position showing the locking mechanism thereof.
FIG. 6B is a close-up detail view of the scalpel handle sheath of FIG. 1 showing an enlargement of the area indicated in FIG. 6A.

As shown in FIGS. 5, 6A, and 6B, body 12 of sheath 10 includes first 54 and second 56 locking channels, with both locking channels 54 and 56 being connected by track 57 having elevated ramps 58 adjacent locking channels 54 and 56. Track 57 and locking channels 54 and 56 engage with tabs 60 of a locking mechanism 62 coupled with shield 30. When the shield 30 is directed towards either the first locking channel 54 or the second locking channel 56, tabs 60 ride over ramps 58, thereby causing inward flexing of locking mechanism 62 by bending of flexible portion 66 thereof (locking mechanism 60 being configured as a cantilevered section integral with shield 30) until tabs 60 snap into either first locking 54 or second locking channel 56, causing an audible signal and a tactual feel indicating that the shield 30 is positively locked in either the retracted position (when locking mechanism 62 is engaged with second locking channel 56) or the extended position (when locking mechanism 62 is engaged with first locking channel 54). It is noted that a set of locking channels 54 and 56 is shown connected by a track 57 on a top surface 68 of body 12, but that a corresponding (or substantially identical) set of locking channels connected by a track can be present on bottom surface 70 of body 12 as well. When shield 30 is locked in either the extended position, as shown in FIGS. 6A and 6B, or the retracted position, as shown in FIG. 5, the locking mechanism 60 may be released by depressing button 64 inward and beginning movement of shield 30 out of such position. The locking mechanism 62 is released when tabs 60 travel beyond the respective locking channels 54 or 56, allowing the shield 30 to be moved either forward or backward.

Figure 7:
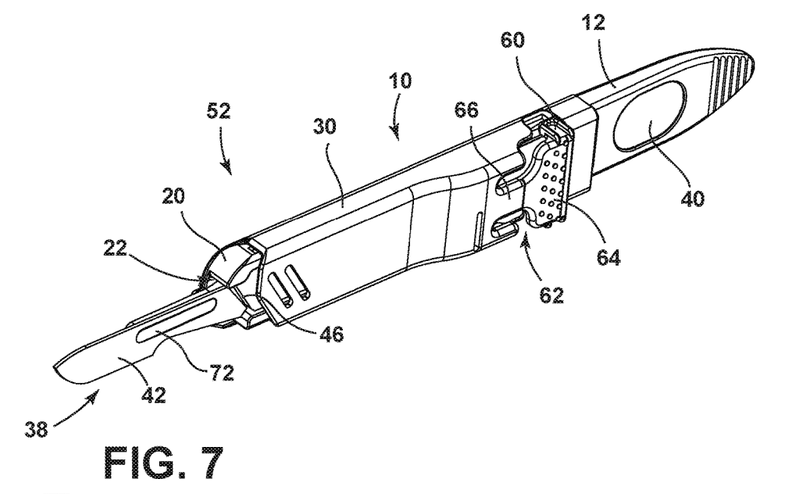
FIG. 7 is a front-right perspective view of the scalpel handle sheath of FIG. 1 in a retracted condition and assembled with a scalpel including a blade.

Sheath 10 is configured such that the blade 42 can be coupled with the blade tang 72 of holder end 44 when the shield 30 is in the retracted position. Such coupling can be done according to generally standard blade loading technique. As shown in FIG. 3, holder end 44 of handle 40 of handle is exposed when shield 30 is in the retracted position. As shown in FIG. 7, blade 42 can be assembled on the handle 40 when shield 30 retracted.

Figure 9:
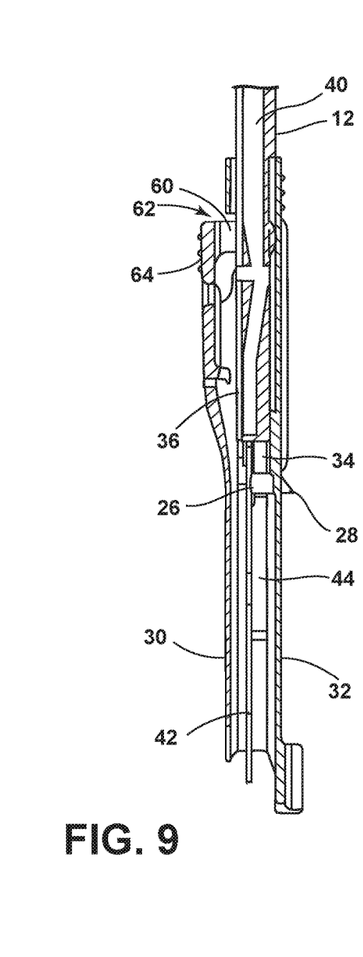
FIG. 9 is a cross-section view of the assembly of FIG. 8, taken along the line IX-IX, showing a removal actuator thereof in a rest position.

As mentioned previously, sheath 10 includes features arranged to execute an "automatic" blade removal. As shown in FIG. 8, a first boss 26 extends inwardly from the resiliently deformable (or flexible) arm 24 that is positioned alongside body 12 adjacent first end 14 of body 12. First boss 26 extends inwardly adjacent to sleeve region 22 and toward a portion of blade 41. When unacted upon, arm 24 is positioned such that first boss 26 extends to a position alongside the blade 42, as further illustrated in FIG. 9. Second boss 28 extends outwardly from arm 24 and is positioned within track 32 of shield 30 throughout at least a portion of the range of motion thereof. In particular, track 32 is positioned such that second boss 28 is unacted upon by shield 30 when shield 30 is retracted and as it is moved from the retracted position toward the extended position. As shown in FIG. 9, just prior to shield 30 reaching the extended position, edge 34 of track 32 contacts second boss 28

Figure 10:
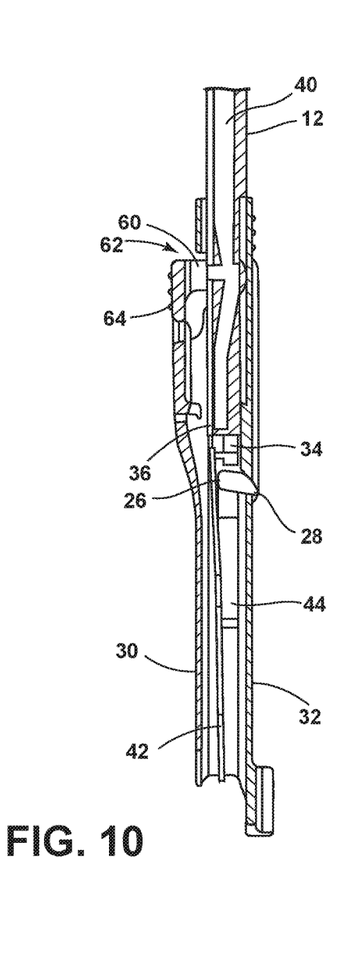
FIG. 10 is a cross-section view of the assembly of FIG. 9, showing the actuator in a cocked position.
Figure 11:
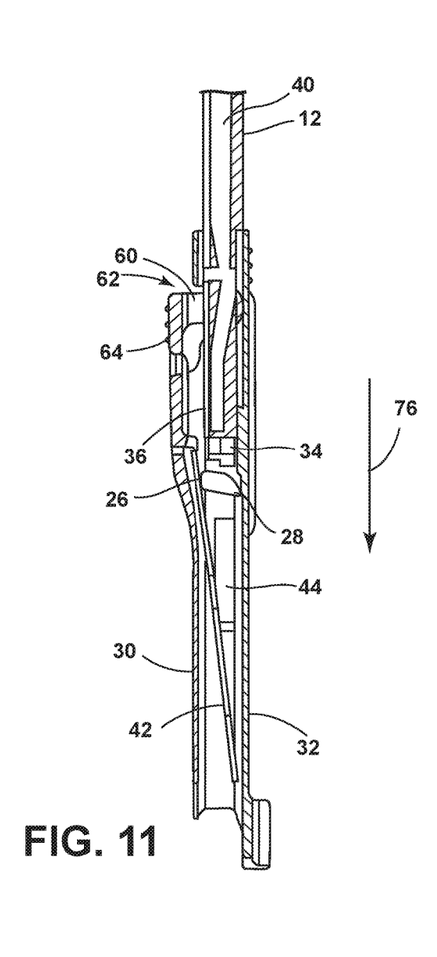
FIG. 11 is a cross-section view of the assembly of FIG. 10 showing the actuator executing a blade removal action along with a removal flange of the sheath.

As shown in FIG. 10, when shield 30 reaches the extended position, edge 34 of moves over and at least begins to depress second boss 28 such first boss 26 pushes the rear edge of the blade 42, which may dislodge a portion thereof from tang 72. In such a condition, if shield 30 is moved back toward the retracted position (i.e. into the condition shown in FIG. 9), the arm 24 and first boss 26 return to their rest ("non-cocked") position which allows the blade 42 to return to a corresponding non-bent condition. Accordingly, blade 42 removal is only achieved when the shield 30 is moved forward from the extended position toward the removal position shown in FIG. 11. This is achieved by pressing the button 64 of locking mechanism 62 inward (in a manner similar to that which is described above) and pushing the shield 30 forward over an additional ramp 78 and into an extension portion 78 of track 57, which are further illustrated in FIGS. 12 and 13 (of which similar portions may be included in a similar track on bottom side 70 of body 12). Such movement results in the removal flange 36 extending within shield 30 to push the blade 42 in direction 76 to completely remove the blade 42 from holder end 44 of the handle 40. As further illustrated in FIG. 11, when blade 42 is removed from handle 40, blade 42 may remain contained within shield 30. This may be facilitated by pressure applied to blade 42 by removal flange 36, causing blade 42 to remain bent. To completely remove the blade 42 from assembly 52, shield 30 can be moved back to the extended position.

Figure 12:
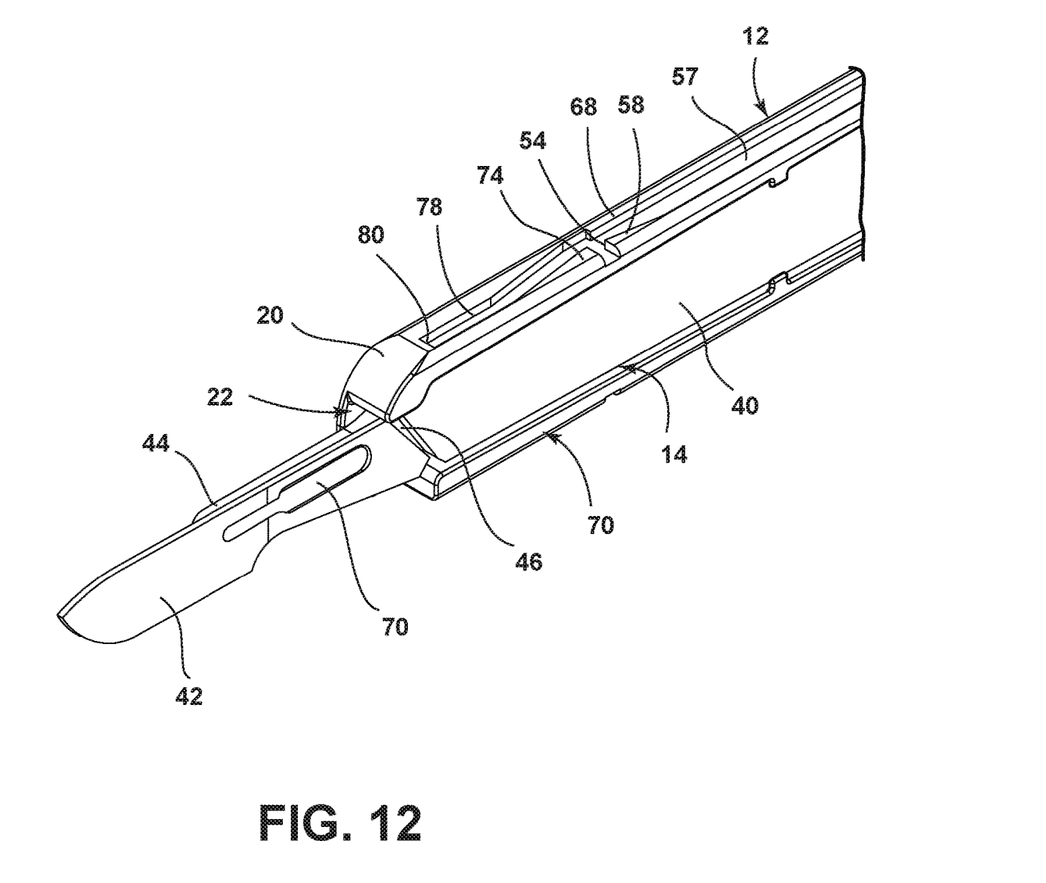
FIG. 12 is a front-right perspective view of the assembly of FIG. 7 with a shield of the sheath removed.
Figure 13:
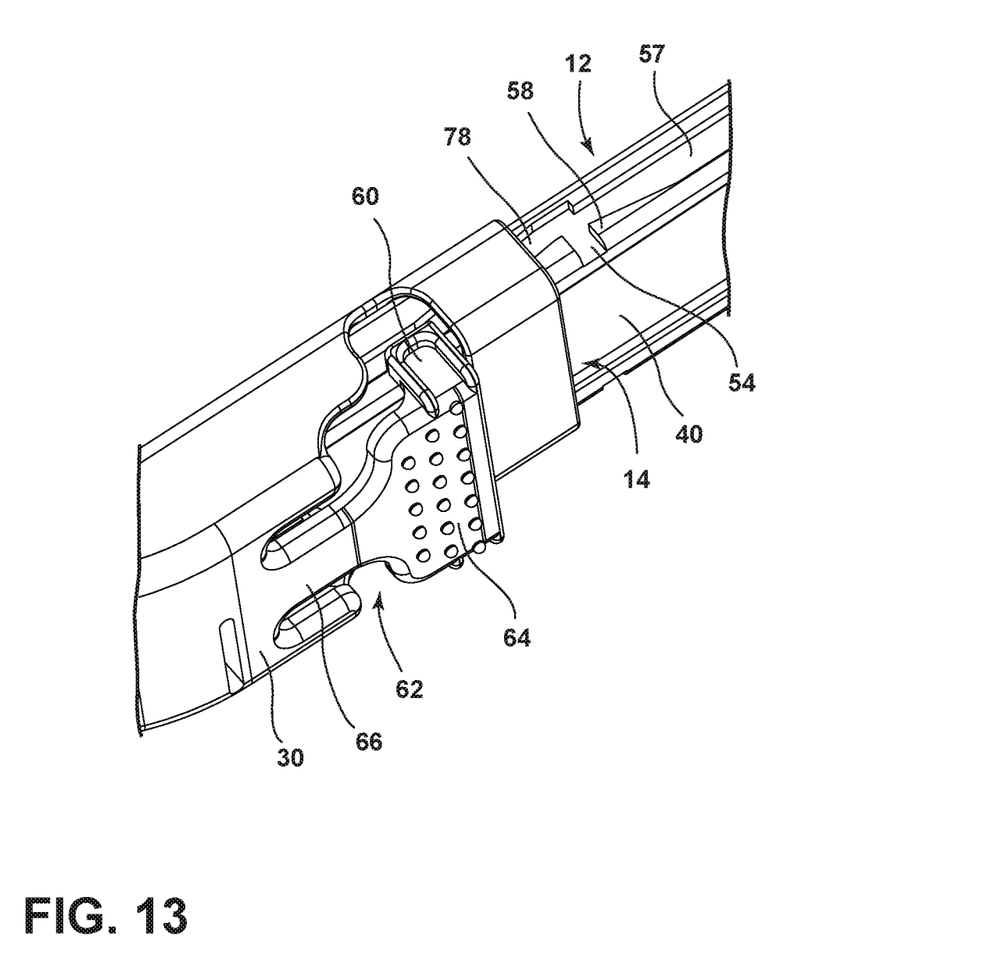
FIG. 13 is a close-up view of the assembly of FIG. 9 in a removal stated and showing a corresponding position of the locking mechanism thereof.

As shown in FIG. 12 secondary portion 78 of track 57 may be located inward of the adjacent portion of track 57 opposite second locking channel 56 therefrom. This can be such that shield 30 is prevented from being moved into the removal position (FIG. 11) unless by depressing of button 64 beyond a position required for movement of shield 30 toward the retracted position. Such positioning of secondary portion 78 may also provide a positive stop for shield 30 when moved into the extended position, preventing premature blade 42 removal during normal use of sheath 10. The purpose of the secondary portion 78 is to allow the shield to furthermore travel horizontally forward when the shield is fully depressed and pushed forward. Further, the secondary portion 78 of track 57 is sloped back outward with is designed such that the orientation of the path is slightly sloped such that the outward biasing of locking mechanism 62 causes tabs 60 to urge shield 30 toward the removal position when engaged with secondary portion 78. It is further shown that an end 80 of track 57 is defined within secondary portion 78. The presence of end 80 may help ensure that the shield 30 does not accidentally become released from the body 12 during blade 42 removal. This feature also ensures prevention of accidental blade removal during use. Shield locking tab shows travel path on blade removal rail on the sheath.

After blade 42 removal, sheath 30 can be moved back to either of the extended or retracted positions. A new blade 42 can be coupled with handle 40, as discussed above, while shield 30 is in the retracted position. If there is no intention to assemble a new blade 42, the handle 40 can be removed from the sheath 10 after the shield 30 is returned to the retracted position. If sheath 10 is intended for single-use, it may then be disposed of. Alternatively, a reusable sheath 10 may be reprocessed or re-sterilized for future use.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A surgical device assembly, comprising:
   a sheath, including:
      a body defining a cavity open to a first end of the body and an arm adjacent the first end, the arm having a first boss extending inwardly therefrom; and
      a shield coupled with the body and slideable between a retracted position and a removal position, the shield defining an edge applying an inward force on the second boss during movement of the shield from the extended position to the removal position and a removal flange extending within the shield and passing the first end of the body during movement of the shield into the removal position; and
   a scalpel including a handle received within the cavity.

2. The surgical device assembly of claim 1, further including a blade, wherein:
   the scalpel handle defines a holder end of the handle extending beyond the first end of the body; and
   the blade is retained on the holder end of the handle and is exposed when the shield is in the retracted position.

3. The surgical device assembly of claim 2, wherein the removal flange further applies a force on the blade in a direction away from the first end of the body of the sheath during sliding into the removal position so as to decouple the blade from the holder end.

4. The surgical device assembly of claim 3, wherein the removal flange applies pressure on the blade when decoupled to retain the blade within the shield.

5. The surgical device assembly of claim 2, wherein the first boss is moveable by flexing of the flexible arm between a first position and a second position, the first boss being positioned away from the blade when the arm is in the first position and applying a bending moment to the blade when the arm is in the second position, the bending moment being below a removal threshold of the blade from the holder end of the handle.

6. The surgical device assembly of claim 2, wherein:
   the shield is further slideable through an extended position between the retracted position and the removal position; and
   the blade is exposed when the shield is in the retracted position and concealed when the shield is in the extended position.

* * * * *